United States Patent [19]

Wagner

[11] Patent Number: 4,996,042

[45] Date of Patent: Feb. 26, 1991

[54] TOOTHPASTE

[75] Inventor: Helmar R. Wagner, Darmstadt, Fed. Rep. of Germany

[73] Assignee: Blendax GmbH, Mainz, Fed. Rep. of Germany

[21] Appl. No.: 336,156

[22] Filed: Mar. 6, 1989

[51] Int. Cl.$^5$ .......................... A61K 9/16; A61K 9/22
[52] U.S. Cl. .......................................... 424/54; 414/57
[58] Field of Search .................. 424/49, 52, 57, 54

[56] References Cited

U.S. PATENT DOCUMENTS

| | | | |
|---|---|---|---|
| Re. 30,309 | 7/1980 | Cousse et al. | 424/52 |
| 3,678,154 | 7/1972 | Widder et al. | 424/52 |
| 4,515,772 | 5/1985 | Parran et al. | 424/57 |
| 4,529,585 | 7/1985 | Hayes | 424/52 |

*Primary Examiner*—Shep K. Rose
*Attorney, Agent, or Firm*—Douglas C. Mohl; Kim William Zerby; Jack D. Schaeffer

[57] ABSTRACT

Toothpaste compositions containing pyrophosphate or phosphonic acid salt and 3 pyridylmethanol, which compositions are effective against calculus.

2 Claims, No Drawings

TOOTHPASTE

The invention refers to a toothpaste which has calculus-reducing activity and keeps the gingiva healthy.

Numerous proposals for actives to be applied in dental and oral care products which are said to have a reducing effect on the calculus (tartar) formation have already been made.

One substance, already extensively investigated in this connection, is ethane 1-hydroxy-1,1-diphosphonic acid (EHDP) which, for the first time, was recommended in the FR-A 1, 514, 194 as a tartar-reducing compound.

In the meantime, commercial use has been made of this proposal as a toothpaste containing this active is on the market since a longer time.

A further group of substances showing strong calculus-reducing efficiency in vitro as well as in vivo is the tetraalkali pyrophosphates, in particular the tetrasodium and tetrapotassium pyrophosphate (W.W. Briner, M.D. Francis. Calc. Tiss. Res. 11 (1973), 10–229.

The EP-A 97, 476 makes use of the findings of this scientific publication and discloses dental and oral care products containing alkali and tetraalkali pyrophosphates in a basis composition which, of course, does not contain compounds releasing calcium ions.

According to clinical investigations, this type of toothpaste achieved an average reduction of tartar formation from about 26 % to about 35 % (see J. Amer. Dental Assoc. 110 (1985), 737–738. and J. Dental Res. 64 (1985). 1159–1162)

It has now been found, and that is the object of the present invention, that an improvement of the gum-caring efficiency of a toothpaste which reduces tartar formation and contains ethane 1-hydroxy-1,1-diphosphonic acid and/or di and/or tetraalkali pyrophosphates can be achieved by the addition of a salt of 3-pyridylmethanol.

3-pyridylmethanol which is also known under the name beta-pyridylcarbinol has a stimulating effect on the blood flow and is used in the form of its salts, in particular tartrates, as a tonic and gum-caring active in dental and oral care products.

It was surprising and not predictable that by combination of these substances an improvement of the gum-caring efficiency is achieved as, according to the present opinion in dental science, no connection exists between the occurence of calculus and gum diseases.

Therefore, it was necessary to take a real inventive selection among the numerous possibilities available and to choose the very limited groups of substances, the joint application of which results in a surprising increase in efficiency in a direction actually not expected and without creating problems of compatibility.

The proportion of ethane 1-hydroxy-1,1-diphosphonic acid in the toothpaste according to the invention is preferably about 0.2 to 2.0 % by weight, in particular between about 0.5 and 1.0 % by weight, calculated to the total composition.

If salts, for example the di and trisodium salt of EHDP, are used, the calculation refers to the proportion of free acid.

Appropriate alkali pyrophosphates are especially disodium, dipotassium as well as tetrasodium and tetrapotassium pyrophosphate and their mixtures.

The proportion of these compounds in the toothpaste according to the invention is between about 1 and 5 % by weight, preferably between 2 and : in particular at about 2.5 to 3.5 % by weight, related to the total composition of the toothpaste, and calculated on the pyrophosphate ion.

According to a preferred method of embodiment, mixtures of EHOP and pyrophosphate(s) can also be applied.

The 3-pyridylmethanol is preferably used in the form of its water-soluble salts.

Particularly suitable are the salts of polybasic carboxylic acids, especially of the (hydrogen) tartrate, but also citrate, gluconate, lactate, aspartate, etc. can be used.

The proportion of the 3-pyridylmethanol salt is about 0.05 to 0.5 % by weight of the total composition, calculated on the free base.

The toothpastes according to the invention should not contain any polishing agents releasing calcium ions to a considerable extent.

Therefore appropriate polishing agents are especially different modifications of silicon dioxide such as precipitated silicagels, silica xerogels and hydrogels, alkalialuminum silicates, e.g. those of the zeolite type as synthetic sodium aluminum silicate of the empiric formula $Na_{12}^{(Al O_2)}{}_{12}^{(Si O_2)}{}_{12}\cdot 27H_2O$, alumina and alumina trihydrate, insoluble metaphosphates, powdered synthetics as well as heat-treated calcium pyrophosphate which practically does not release any calcium ions.

Mixtures of polishing agents from the substances mentioned above of course can also be used, for example the mixture of -alumina trihydrate and/or of insoluble alkalimetaphosphate and synthetic zeolite A in a ratio of about 1:1.

The proportion of polishing agents in the toothpastes according to the invention is preferably between about 20 and 60 % by weight of the total composition.

It is obviously possible to apply the common surface-active compounds used in toothpastes in quantities up to about 2.5 % by weight of the total composition.

Such synthetic surface-active agents are for example alkyl sulfates. alkyl ethersulfates. olefin sulfonates, sodiumlauroyl sarcosinate or ampholytic, non-ionic or cation-active compounds or also soaps as for example sodium salts of lauric acid. myristic acid, palmitic acid, stearic acid or their mixtures as for example coconut oil fatty acids or tallow fatty acids.

The toothpaste according to the invention contains conventional moisturizing agents usually used in toothpastes in quantities of about 10 to 35 % by weight. such as glycerin, diols, e.g. 1,4-butanediol or 1.2propanediol or sugar alcohols such as sorbitol, mannitol, or xylitol and polyglycols with low molecular weights.

Preferred thickening agents usually present from about 0.25 to about 2.5 % by weight are carboxymethylcellulose and its alkali salts, especially sodium carboxymethylcellulose, hydroxyalkylcelluloses such as hydroxymethylcellulose and hydroxycellulose, methylcellulose, plant gums such as tragacanth, Arabic gum, caraya gum, guar gum, xanthan gum and Irish moss, synthetic polyelectrolytes such as the amine and alkali salts of the polyacrylic acid as well as inorganic thickening agents, for example colloidal magnesium aluminum silicate or silica.

Of course, other actives can also be used in the toothpastes according to the invention. Those are especially the well-known, caries-prophylactic fluorides, preferably in such a quantity that the concentration of pure fluoride is about 0.05 to 1 % per weight, preferably 0.1 to 0.5 % by weight of the total composition.

Appropriate fluorine compounds are especially the various salts of the monofluorophosphoric acid such as sodium, potassium, lithium, calcium and aluminum mono- and difluorophosphates as well as different ionic fluorides, particularly alkali fluorides such as sodium, lithium, potassium and ammonium fluoride, stannous fluoride, manganese fluoride, copper. zirconium and aluminum fluoride as well as mixtures or addition products of these fluorides between each other and with other fluorine compounds, for example alkali manganese fluorides.

Further compounds applicable in toothpastes according to the invention are actives to prevent dental plaque formation such as chlorhexidine salts, zinc and copper compounds, urea, hexetidin, hesperidin, allantoin, azulen and other substances further preventing or reducing calculus formation such as alkylenediaminotetra(methylenphosphonic acids), etc.

The pH-value of the toothpaste according to the invention is between about 4 and 10, preferably 5.5 and 9.0.

A summary of substances used in toothpastes and compounds and measures which are usually required for the production of dental care products is given in the monography "Cosmetics - Science and Technology", 2nd ED., Vol. 1, page 423 to 533 (1972) by M.S. Balsam and E. Sagarin, which is included by reference.

The following examples illustrate the present invention:

EXAMPLE 1

| | |
|---|---|
| α-alumina trihydrate | 38.00 (% by weight) |
| sorbitol | 10.00 |
| glycerin | 5.00 |
| methylcellulose | 0.80 |
| hydroxyethylcellulose | 0.40 |
| sodium monofluorophosphate | 0.76 |
| sodium fluoride | 0.11 |
| sodium laurylsulphate | 1.20 |
| flavor mixture | 1.00 |
| saccharin sodium | 0.08 |
| colloidal silica | 0.50 |
| methyl p-hydroxybenzoate, sodium salt | 0.25 |
| β-pyridylmethanol hydrogentartrate | 0.15 |
| EHDP, trisodium salt | 0.85 |
| tetrasodium pyrophosphate | 3.75 |
| allantoin | 0.25 |
| water | ad 100.00 |

EXAMPLE 2

| | |
|---|---|
| precipitated silicagel | 23.50 (% by weight) |
| silica aerogel | 2.50 |
| glycerin | 9.00 |
| sorbitol | 17.50 |
| sodium laurylsulphate | 1.50 |
| carboxymethylcellulose | 1.25 |
| sodium fluoride | 0.25 |
| flavor mixture | 1.10 |
| saccharin sodium | 0.05 |
| copper sulphate . 5H$_2$O | 0.25 |
| hexetidin | 0.05 |
| methyl p-hydroxybenzoate, sodium salt | 0.20 |
| n-propyl p-hydroxybenzoate, sodium salt | 0.10 |
| 3-pyridylmethanol tartrate | 0.20 |
| tetrapotassium pyrophosphate | 3.10 |
| water | ad 100.00 |

EXAMPLE 3

| | |
|---|---|
| insoluble sodium metaphosphate | 38.00 (% by weight) |
| sorbitol | 13.00 |
| colloidal silica | 2.80 |
| hydroxyethylcellulose | 1.80 |
| methyl p-hydroxybenzoate | 0.10 |
| benzoic acid | 0.10 |
| saccharin sodium | 0.20 |
| flavor mixture | 1.10 |
| fatty alcohol polyglycolether | 0.60 |
| 1,2-propanediol | 4.00 |
| titanium dioxide | 0.80 |
| N,N',N'-tri(2-hydroxyethyl) N-octadecyl 1,3-diaminopropane dihydrofluoride | |
| 3-pyridylmethanol dihydrogencitrate | 0.25 |
| EHDP, disodium salt | 1.60 |
| water | ad 100.00 |

EXAMPLE 4

| | |
|---|---|
| polymethyl methacrylate powder (medium particle size 1–5 μm) | 15.00 (% by weight) |
| heat-treated β-calcium pyrophosphate | 15.00 |
| sodium carboxymethylcellulose | 1.20 |
| sodium laurylsarcosinate | 0.80 |
| sodium laurylsulphate | 0.80 |
| sodium monofluorophosphate | 1.20 |
| saccharin sodium | 0.10 |
| flavor mixture | 1.10 |
| 3-pyridylmethanol gluconate | 0.30 |
| tetrasodium pyrophosphate | 3.20 |
| EHDP, disodium salt | 0.60 |
| glycerin | 10.00 |
| sorbitol | 8.00 |
| water | ad 100.00 |

EXAMPLE 5

| | |
|---|---|
| silica xerogel | 25.00 (% by weight) |
| silica aerogel | 2.80 |
| sorbitol | 35.00 |
| xanthan gum | 1.10 |
| sodium fluoride | 0.30 |
| EHDP, disodium salt | 0.80 |
| disodium pyrophosphate | 1.00 |
| 3-pyridylmethanol tartrate | 0.10 |
| tetrasodium pyrophosphate | 1.80 |
| sodium laurylsulphate | 1.30 |
| sodium lauroylsarcosinate | 0.80 |
| flavor mixture | 1.00 |
| saccharin sodium | 0.10 |
| methyl p-hydroxybenzoate, sodium salt | 0.30 |
| dye solution | q.s. |
| water | ad 100.00 |

EXAMPLE 6

| | |
|---|---|
| calcined β-calcium pyrophosphate | 45.00 (% by weight) |
| insoluble sodium metaphosphate | 15.00 |
| glycerin | 5.50 |
| sorbitol | 12.50 |
| sodium carboxymethylcellulose | 1.20 |
| sodium sulforicinoleate | 0.80 |
| sodium laurylsulphate | 1.20 |
| 3-pyridylmethanol tartrate | 0.25 |
| tetrasodium pyrophosphate | 4.00 |
| disodium pyrophosphate | 1.20 |
| sodium monofluorophosphate | 1.14 |
| saccharin sodium | 0.11 |
| flavor mixture | 1.00 |

| | |
|---|---|
| -continued | |
| sodium benzoate | 0.30 |
| methyl p-hydroxybenzoate, sodium salt | 0.15 |
| water | ad 100.00 |

We claim:

1. A toothpaste being basically free from compounds releasing calcium ions, characterized by containing a combination of
    (a) an anticalculus agent selected from the group consisting of an alkali metal pyrophosphate sufficient to provide about 1% to about 5% pyrophosphate ions based on the total composition, ethane 1-hydroxy-1,-1,-diphosphonic acid or its water soluble salts sufficient to provide about 0.2 to about 2.0% of phosphonic acid based on the total composition and mixtures thereof and
    (b) a water-soluble salt of 3-pyridylmethanol in a quantity of 0.05 to 0.5% by weight (calculated on 3-pyridylmethanol), related to total composition.

2. A toothpaste according to claim 1, characterized by containing the tartrate salt of 3-pyridylmethanol.

* * * * *